United States Patent
Speck et al.

(10) Patent No.: US 7,001,420 B2
(45) Date of Patent: Feb. 21, 2006

(54) COIL REINFORCED MULTILAYERED INNER TUBULAR MEMBER FOR A BALLOON CATHETER

(75) Inventors: Marc L. Speck, Temecula, CA (US); Sharon Wong, Ithaca, NY (US); Jeong S. Lee, Diamond Bar, CA (US); Matthew Chludzinski, Poway, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 454 days.

(21) Appl. No.: 10/279,648

(22) Filed: Oct. 24, 2002

(65) Prior Publication Data
US 2004/0002728 A1 Jan. 1, 2004

Related U.S. Application Data

(63) Continuation-in-part of application No. 10/186,789, filed on Jul. 1, 2002.

(51) Int. Cl.
*A61F 2/06* (2006.01)

(52) U.S. Cl. .................. 623/1.11; 604/103.09; 606/194

(58) Field of Classification Search ............... 606/194, 606/108; 604/103.09; 623/1.11
See application file for complete search history.

(56) References Cited

U.S. PATENT DOCUMENTS

| | | | |
|---|---|---|---|
| 4,981,478 A | 1/1991 | Evard et al. | |
| 5,728,065 A | 3/1998 | Follmer et al. | |
| 5,951,539 A | 9/1999 | Nita et al. | |
| 6,165,163 A | 12/2000 | Chien et al. | |
| 6,319,228 B1 * | 11/2001 | Kastenhofer | 604/96.01 |
| 6,511,462 B1 | 1/2003 | Itou et al. | |
| 6,669,886 B1 * | 12/2003 | Willard | 264/171.14 |
| 2004/0002727 A1 | 1/2004 | Hwang et al. | |

* cited by examiner

Primary Examiner—(Jackie) Tan-Uyen T. Ho
(74) Attorney, Agent, or Firm—Fulwider Patton LLP

(57) ABSTRACT

A catheter having an elongated shaft formed of a polymeric tubular member with at least a section having a lubricious inner layer defining the guidewire lumen, a coiled support member at least partially embedded in the lubricious inner layer, and an outer layer on an outer surface of at least a distal portion of the lubricious inner layer. In a presently preferred embodiment, the coil supported polymeric tubular member forms an inner tubular member of a balloon catheter.

19 Claims, 3 Drawing Sheets

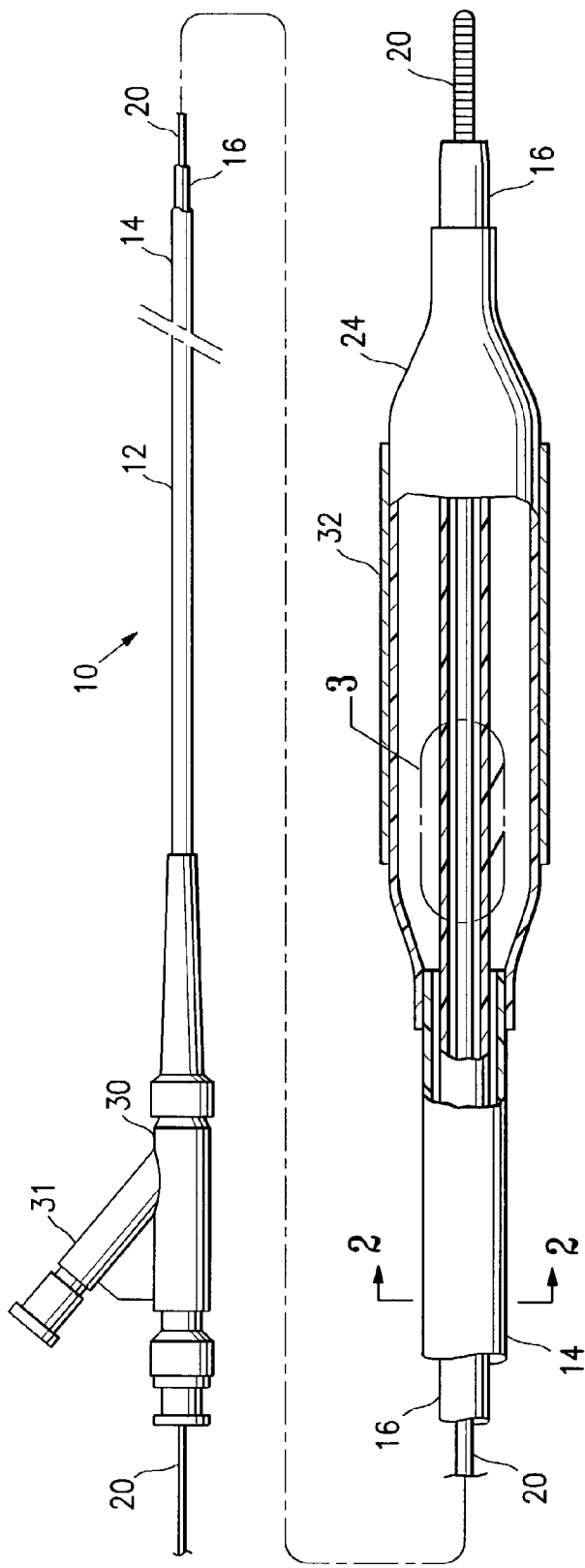
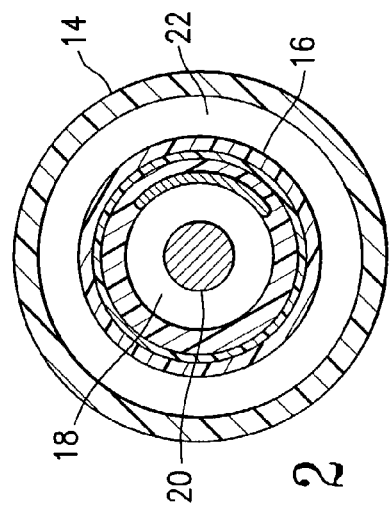
FIG. 1
FIG. 2

COIL REINFORCED MULTILAYERED INNER TUBULAR MEMBER FOR A BALLOON CATHETER

This is a continuation-in-part of prior pending application, U.S. Ser. No. 10/186,789, filed Jul. 1, 2002 for COIL REINFORCED CATHETER INNER TUBULAR MEMBER.

BACKGROUND OF THE INVENTION

This invention generally relates to catheters, and particularly intravascular catheters for use in percutaneous transluminal coronary angioplasty (PTCA) or for the delivery of stents. In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau, et al.) and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter) and flexibility to be readily advanceable within the tortuous anatomy of the patient's vasculature. Conventional balloon catheters for intravascular procedures, such as angioplasty and stent delivery, frequently have relatively a stiff proximal shaft section to facilitate advancement of the catheter within the patient's body lumen and a relatively flexible distal shaft section to facilitate passage through tortuous anatomy such as distal coronary and neurological arteries without damage to the luminal wall.

To help meet the desire for a catheter having sufficient pushability, while maintaining trackability, prior art designs have supplemented polymer catheter shafts with a stiffening wire or mandrel. Other prior art designs have addressed these handling and performance issues by suggesting use of materials of different stiffness or reinforcements in the proximal and distal portions of the catheter shaft. Despite these attempts, prior art designs have suffered from various drawbacks. For example, one difficulty has been providing a flexible inner tubular member (defining a guidewire lumen of a balloon catheter) which does not readily collapse under elevated inflation pressures. A collapsed inner tubular member prevents or inhibits movement of the guidewire after inflation of the balloon, thus forcing the practitioner to remove the whole catheter system from the patient's body lumen, losing position of the guidewire therein.

Accordingly, it would be a significant advance to provide a catheter having a thin walled yet highly collapse resistant tubular member while maintaining good flexibility. This invention satisfies these and other needs.

SUMMARY OF THE INVENTION

The invention is directed to a catheter having an elongated shaft formed of a polymeric tubular member with at least a section having an lubricious inner layer defining the guidewire lumen, a coiled support member at least partially embedded in the lubricious inner layer, and an outer layer on an outer surface of at least a distal portion of the lubricious inner layer. In a presently preferred embodiment, the coil supported polymeric tubular member forms an inner tubular member of a balloon catheter.

The coiled support member is preferably formed of a wire or ribbon wound into a coiled configuration to provide excellent flexibility. In one embodiment, a bare wire or ribbon is wound into the coiled configuration and is then covered with a multilayered polymeric tube to form the coil supported polymeric tubular member. Specifically, the wound coil is placed in the lumen of a multilayered polymeric tube, and the assembly heated, so that the coil becomes at least partially embedded in a lubricious inner layer of the multilayer tube. The inner layer of the multilayered polymeric tube, before the multilayered polymeric tube is heated over the coil to partially embed the coil therein, has a wall thickness of about 0.0005 to about 0.003 inches, and preferably about 0.001 inches, and the resulting coil supported multilayered tube (after the multilayered tube is heated down around the coil) has a coil partially embedded in a lubricious inner layer (the lubricious inner layer having a wall thickness of about 0.001 to about 0.003 inches).

In an alternative embodiment, the coiled support member is coated with a lubricious polymeric material before being wound into the coiled configuration. This lubricious polymeric coating is heated during assembly of the shaft to fuse together and at least in part form the lubricious inner layer of the shaft. Before being heated during assembly of the shaft, the thickness of the coating on the coil is about 0.0003 to about 0.002 inches. The resulting coil supported tubular member (after the coating is heated to flow and fuse together to form a lubricious inner layer of the coil supported tubular member) has a coil completely embedded in the lubricious inner layer (the lubricious inner layer having a wall thickness of about 0.001 to about 0.003 inches). This lubricious inner layer has a small wall thickness of precise dimensions, providing improved catheter performance and manufacturability. The coating on the coil provides a lubricious layer with a completely embedded coil. Additionally, the lubricious layer produced by the coating on the coil is thinner than would be readily produced by winding a bare coil on an outer surface of an extruded lubricious layer. In one embodiment, the coils of the coated coiled support member are spaced apart. In order to fill the spaces between the spaced apart coated coils with lubricious material, a lubricious polymeric tube, preferably formed of the same material as the coating on the wire or ribbon, is positioned around an outer surface of the wound wire or ribbon during assembly of the shaft. In another embodiment, the coils of the coated coiled support member are stacked together, and the lubricious polymeric coating on the wire or ribbon alone forms the inner lubricious layer of the shaft. Unlike a bare coil, the precoated coil does not have to be forced into a polymeric layer during manufacture of the coil supported polymeric tube. As a result, the potential for movement or bunching of the coil during manufacture or after manufacture is reduced. For example, the tendency of the coil to separate from the polymer and tangle with the guidewire is reduced due to the consistent embedment depth of the coil in the polymer. Also, in the case of closed wound coils, the coil spacing in the finished product is very consistent and more robust because the polymer that covers the wire controls the pitch, and rough handling during assembly cannot decrease the wire spacing. Moreover, the coils fully coated with the polymer eliminate the potential for the guidewire to rub on the metal surface of the coils, to thereby provide good guidewire movement in the coil supported polymeric tube.

The lubricious inner layer is preferably a highly lubricious material such as high density polyethylene (HDPE), although a variety of lubricious polymeric materials may be used including HDPE blended with PLEXAR, and fluoropolymers such a polytetrafluoroethylene (PTFE) (which may be etched to improve bonding).

The outer layer on the outer surface of the lubricious inner layer may comprise multiple layers, or multiple materials blended together. Preferably, the outer layer is fusion bondable to the inner lubricious layer, and provides an outer surface fusion bondable to other catheter components such as a balloon or a distal tip member. The outer layer is a single or multilayered polymeric tubular member which is heat shrunk onto the lubricious inner layer or coextruded with the lubricious inner layer. In one embodiment the outer layer is formed of a polymeric material selected from the group consisting of polyamides, polyether block amides, functionalized polyolefins, and polyurethanes.

In one embodiment, the coil supported polymeric tubular member has an intermediate layer on an outer surface of the lubricious inner layer, located between the lubricious inner layer and the outer layer. The intermediate layer is preferably a polymeric material fusion bondable to the lubricious polymeric material of the inner layer and the polymeric material of the outer layer. For example, in a presently preferred embodiment, the intermediate layer is formed of a functionalized polyolefin such as PRIMACOR, available from DOW Chemical Company, PLEXAR, available from Equistar Chemicals, LP, or BYNEL (modified ethylene vinyl acetate polymer), available from E.I. du Pont de Nemours and Company.

The outer layer(s) can have a length equal to, less than, or greater than the lubricious inner layer, and may extend beyond one or both ends of the coil to provide a non-reinforced area (i.e., not reinforced by the coil) as for example at the area of the distal tip or the rapid exchange guidewire proximal port. In one embodiment, the outer layer(s) extend the entire length of the lubricious inner layer. In an alternative embodiment, the outer layer is located on a distal and/or proximal end portion of the lubricious inner layer, in sufficient length to provide a bonding surface for fusion bonding the coil supported tubular member to, for example, the balloon at the distal end and a shaft section at the proximal end. The profile of the coil supported tubular member is therefore decreased on the portions not having the outer layer, with corresponding benefits on shaft performance characteristics, such as decreased inflation/deflation time. The coil and the inner lubricious layer are therefore configured in one embodiment to provide sufficient collapse resistance in the proximal portions of the coil supported polymeric tubular member, despite the absence of the outer layer(s). The proximal portions, formed only by the coil supported lubricious layer, have a wall thickness of about 0.001 to about 0.002 inches, preferably about 0.001 to about 0.0015 inches.

The coil supported tubular member has an improved high collapse pressure despite its small wall thickness, for improved collapse resistance during inflation of the catheter balloon. For example, in one embodiment, the coil supported tubular member of the invention has a collapse resistance of at least about 24 atm, preferably at least about 30 atm (i.e., in a test method in which a coil supported tubular member having an inner diameter of about 0.016 to 0.0165 inches is subjected to a radially collapsing pressure of about 24 to about 30 atm on the outer surface thereof, a mandrel or guidewire having an outer diameter of about 0.014 inches can be freely moved longitudinally within the tubular member lumen with reasonable force). Additionally, the inner surface is highly lubricious, providing improved movement of devices such as a guidewire in the lumen. Although the dimensions of the coil supported tubular member will be scaled according to the final catheter shaft dimensions, for a typical coronary angioplasty catheter with dilatation balloon diameter sizes of about 1.5 mm to about 5 mm, the final wall thickness of the coil supported tubular member forming the inner tubular member of a balloon catheter is about 0.0015 to about 0.004 inches, preferably about 0.002 to about 0.003 inches. Additionally, in one embodiment, the coiled supported tubular member has an inner diameter of about 0.014 to about 0.0165 inches and an outer diameter of about 0.02 to about 0.0225 inches, for a typical coronary angioplasty catheter (with dilatation balloon diameter sizes of about 1.5 mm to about 5 mm).

In a presently preferred embodiment, the catheter is a balloon catheter, and preferably a coronary angioplasty balloon catheter having an inflated balloon diameter of about 1.5 to about 5 mm. However, the balloon catheter of the invention may comprise a variety of suitable balloon catheters, including coronary and peripheral dilatation catheters, stent delivery catheters, drug delivery catheters, and the like. A balloon catheter of the invention generally comprises an elongated shaft with an inflation lumen, a guidewire receiving lumen, a proximal shaft section defining a proximal portion of the inflation lumen, and a distal shaft section defining a distal portion of the inflation lumen, with an inflatable balloon on the distal shaft section having an interior in fluid communication with the inflation lumen. At least part of the guidewire receiving lumen extends within the distal shaft section to a guidewire distal port in the distal end thereof. In one embodiment, the catheter is a rapid exchange type catheter having a guidewire distal port at the distal end of the catheter, a guidewire proximal port in the distal shaft section spaced a relatively short distance proximally from the guidewire distal port and a relatively long distance from the proximal end of the catheter shaft, and a relatively short guidewire receiving lumen extending between the proximal and distal guidewire ports in the distal shaft section. In an alternative embodiment, the catheter is an over-the-wire type catheter having an elongated shaft with proximal and distal ends, a guidewire port in the proximal end, a guidewire port in the distal end, and a guidewire lumen extending therein from the distal end to the proximal end of the catheter shaft. For the over-the-wire type catheters, the present invention may form all or only a portion of the guidewire lumen, and specifically, in one preferred embodiment, a distal portion of the guidewire lumen.

In a presently preferred embodiment, the balloon catheter elongated shaft comprises an outer tubular member defining an inflation lumen, and an inner tubular member within the outer tubular member lumen and defining a guidewire lumen, and the coil supported polymeric tube of the invention forms the inner tubular member. The coiled supported inner tubular member is a low profile tubular member with excellent collapse resistance.

In one embodiment, the coiled support member is a wire member having a round or oval cross section, although a variety of cross sectional shapes may be used including a flat member such as a ribbon. The coiled support members are preferably formed of a high modulus material such as metal, carbon fiber, and polymeric materials such as Kevlar and liquid crystal polymers including Vectran. In a presently preferred embodiment, the coiled support member is formed of a metal such as a stainless steel, or super elastic alloy including a nickel-titanium (Nitinol) alloy. The coiled support member can be formed of multiple strands of wire or ribbon. In a presently preferred embodiment for a coronary angioplasty catheter, the coiled support member is a fine gauge wire having an outer diameter of about 0.0005 to about 0.002 inches, preferably about 0.0005 to about 0.001 inches, or a fine gauge ribbon having a width of about 0.0025 to about 0.007 inches, preferably about 0.0035 inches, and a height of about 0.0005 to about 0.001 inches, preferably about 0.00075 inches.

The coil supported polymeric tubular member of the invention has a highly lubricious inner surface, high collapse pressure, and pushability despite the thin wall thickness of the tubular member. In the embodiment in which the wire or ribbon is precoated with the lubricious polymeric material before being wound into a coiled configuration, the lubricious layer has a very thin, repeatable wall thickness. Consequently, the catheter of the invention is flexible and collapse resistant under high pressure, with good guidewire movement in the guidewire lumen. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter which embodies features of the invention, having an inner tubular member formed of a trilayer extruded tube heated onto a bare, wound wire.

FIG. 2 is a transverse cross sectional view of the catheter shown in FIG. 1, taken along line 2—2.

DETAILED DESCRIPTION OF THE INVENTION

Figure 3:
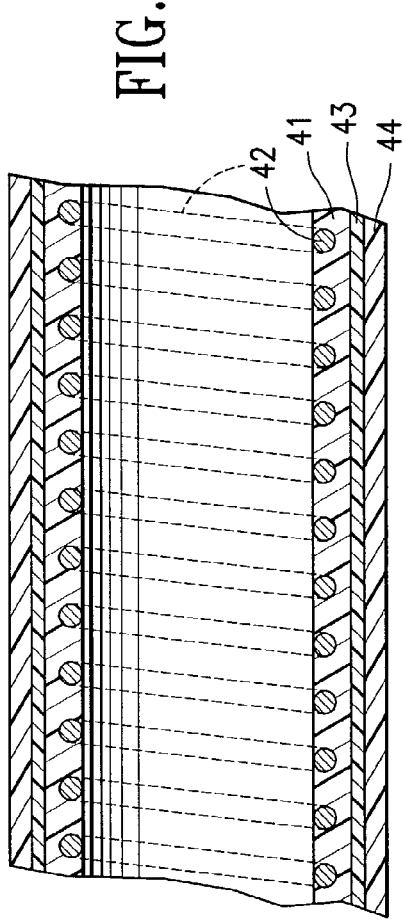
FIG. 3 is an enlarged, longitudinal cross sectional view of the catheter shown in FIG. 1, taken along line 3—3.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20. The coaxial relationship between outer tubular member 14 and inner tubular member 16 defines annular inflation lumen 22, as best illustrated in FIG. 2 showing a transverse cross section view of the distal end of the catheter shown in FIG. 1, taken along line 2—2. An inflatable balloon 24 disposed on a distal section of catheter shaft 12 has a proximal skirt section sealingly secured to the distal end of outer tubular member 14 and a distal skirt section sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. In FIG. 1, balloon 24 is illustrated prior to complete inflation thereof, with an expandable stent 32 mounted on uninflated balloon 24. The distal end of the catheter may be advanced to a desired region of a patient's body lumen in a conventional manner and balloon 24 inflated to expand stent 32, and the balloon 24 deflated and the catheter withdrawn, leaving the stent 32 implanted in the body lumen.

FIG. 3 illustrates an enlarged, longitudinal cross sectional view of the inner tubular member 16 of the catheter 10 shown in FIG. 1, taken within circle-3. In the embodiment of FIG. 3, inner tubular member 16 comprises a coil supported polymeric tube with a lubricious polymeric inner layer 41, a coiled support member 42 in the inner layer 41, an intermediate polymeric layer 43 on an outer surface of the inner layer 41, and an outer polymeric layer 44 on an outer surface of the intermediate layer 43. In the illustrated embodiment, the intermediate and outer layers 43, 44 extend the entire length of inner layer 41 and coiled support member 42. In alternative embodiments (not shown), the intermediate and outer layers 43, 44 are on a distal portion of the shaft, between the balloon and the shaft, and are not on the entire length of the inner layer 41 coiled support member 42, or alternatively, extend beyond one or both ends of the coil to form non-reinforced sections of the shaft.

In a presently preferred embodiment, the lubricious inner layer 41 is high density polyethylene (HDPE). The intermediate layer 43 is preferably an ethylene based adhesive polymeric such as PRIMACOR, and the outer layer 44 is preferably a polymer fusion bondable to the polymeric material of the balloon and in one embodiment is a nylon, or copolyamide such as PEBAX, or a polyurethane. The three polymeric layers 41, 43, 44 are preferably a trilayer extrusion formed by extruding the three layers together. The outer layer may have variable stiffness along the length thereof.

In the embodiment illustrated in FIG. 3, the coiled support member 42 is a wire, with spaced apart coils. In a presently preferred embodiment, the wire has a diameter of about 0.0003 to about 0.001 inches, and the spaced apart coils have an intercoil spacing of at most about 0.015 inches, preferably at most about 0.010 inches. In the embodiment illustrated in FIG. 3, the coiled support member 42 is partially embedded in the inner layer 41. The terminology "partially embedded" should be understood to mean that at least part of the inner coiled support member is not covered by the polymeric material of the inner layer 41. In the embodiment illustrated in FIG. 3, an inner surface of the support member 42 directed toward the lumen 18 of the inner tubular member 16 is not covered by the polymer of the inner layer 41.

Figure 4:
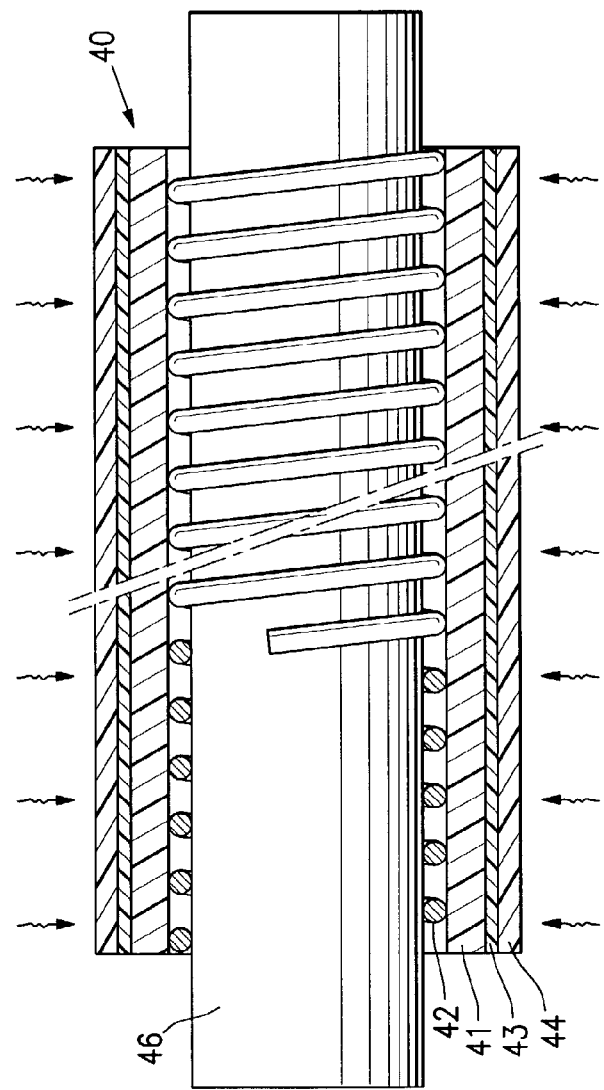
FIG. 4 illustrates a partially in section view of an assembly during formation of the tubular member of FIG. 3.

In one embodiment, the coil supported tubular member of FIG. 3 is formed by placing the trilayer tubing 40 (which forms the inner, intermediate, and outer layers 41, 43, 44 of the coil supported polymeric tube), over the coil 42, and heating the assembly (preferably with heat shrink tubing (not shown) therearound, to at least partially embed the coil 42 in the inner layer 41. FIG. 4 illustrates an assembly of the coil 42 wound on a mandrel 46, with the trilayer tubing 40 slid over the coil and mandrel, prior to heating the assembly. The assembly is heated, as for example in an oven or by traversing a heating nozzle along the length of the polymeric tubing, (at a heated air temperature of about 400° F. to about 500° F.). During heating, heat shrink tubing, if present, shrinks, and the outer layer 44 typically shrinks, and the polymeric layers 41, 43, 44 soften, so that the inner layer flows onto and around the exposed surface of the coil 42. The wall thickness of the inner lubricious layer 41 is about 0.0002 to about 0.003 inches, preferably about 0.0005 to about 0.002 inches, for a coil 42 formed of a ribbon having a width of about 0.0035 inches and a thickness of about 0.00075 inches.

Figure 5:
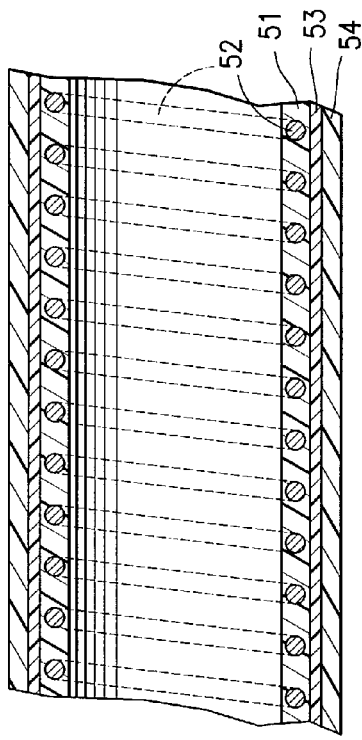
FIG. 5 is an enlarged, longitudinal cross sectional view of an alternative embodiment of an inner tubular member, formed using a precoated coiled support member.
Figure 6:
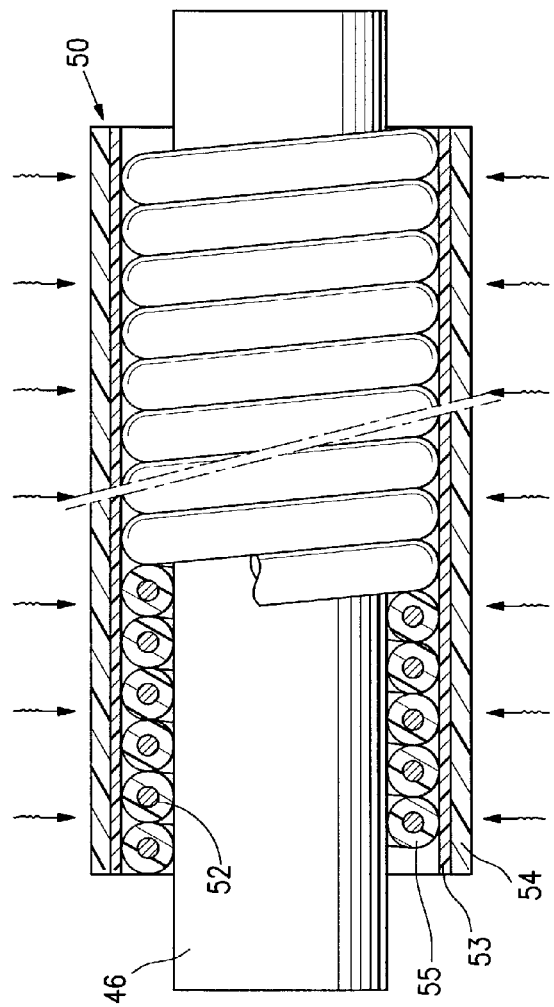
FIG. 6 illustrates a partially in section view of an assembly during formation of the tubular member of FIG. 5.

FIG. 5 illustrates an alternative embodiment of the inner tubular member 16 of the catheter of FIG. 1, in which the coiled wire is completely embedded in the inner layer. As in the embodiment of FIG. 3, the coil supported tubular member of FIG. 5 comprises a lubricious polymeric inner layer 51, a coiled support member 52 in the inner layer 51, an intermediate polymeric layer 53 on an outer surface of the inner layer 51, and an outer polymeric layer 54 on an outer surface of the intermediate layer 53. FIG. 6 illustrates one method of making the coil supported tubular member of FIG. 5, in which wire 52 having a lubricious polymeric coating 55 thereon is wound on mandrel 46. The coated wire 52 on the mandrel 46 is placed in the lumen of a multilayer polymeric tubular member 50, and the assembly is heated, to form the coil supported polymeric tube of FIG. 5. The lubricious polymeric coating 55 on the wire 52 flows and fused together during heating of the assembly, to form the lubricious inner layer 51 of the coil supported tubular member. The lubricious polymeric coating 55 on the wire 52 (see FIG. 6) has a wall thickness of about 0.0003 to about 0.002 inches. After being heated, the total wall thickness of the inner lubricious layer 51 of the coil supported tubular member (see FIG. 5) is about 0.001 to about 0.003 inches. For example, in one embodiment, the total wall thickness of the inner lubricious layer 51 is about 0.0015 inches for a coil 52 having a diameter of about 0.001 inches. In the embodiment of FIG. 6, the coated wire 52 has stacked coils (i.e., with the outer coated surfaces placed together). In an alternative embodiment, the coated wire 52 has spaced apart coils (not shown). In one embodiment in which the spaced apart coated coils are spaced too far apart for the lubricious coating 55 to fuse together to completely form the inner layer 51, a lubricious polymeric layer of a tubular member is heated on the coated coil 52 to in part form the lubricious inner layer 51. Thus, the coating 55 on the coil in part forms the inner layer 51, and the space between the coils is filled with additional lubricious material as for example from a lubricious layer or coating applied on the wound coated coil 52. For example, in one embodiment, a trilayer polymeric tubular member having a lubricious inner layer would be used instead of the dual layer polymeric tubular member 50 illustrated in FIG. 6. Similarly, a separate lubricious polymeric sleeve (not shown) is placed between the wound coated coil 52 and the dual layer polymeric tubular member 50 before the assembly is heated. The separate lubricious sleeve is preferably formed of the same material as the lubricious coating 55 on the coil 52, and is typically relatively thin with a wall thickness of about 0.0001 to about 0.002 inches. Alternatively, the coated wound coil 52 is coated with a dispersion of the lubricious material to fill the spaces between the coils.

Similar to the embodiment of FIG. 3, the polymeric tubular member 50 forming layers 53, 54 extends substantially the entire length of the coil 52. In an alternative embodiment (not shown), polymeric tubular member 50 forming layers 53, 54 is located only at proximal and/or distal end sections of coil 52. Outer layer 54 is preferably a polymeric material selected to facilitate fusion bonding the balloon distal skirt section to the inner tubular member 16, and in one embodiment is selected from the group consisting of PRIMACOR, PLEXAR, BYNEL, PEBAX, polyurethanes, and a polyamide such as nylon 12.

When the catheter of the invention is used in an angioplasty procedure, the balloon catheter of the invention is advanced over the guidewire until the balloon is properly positioned across the stenosis within the patient's body lumen. The balloon can be inflated in a conventional manner by introducing inflation fluid through the inflation lumen. After one or more inflations, the balloon is deflated and the catheter removed from the patient. A similar procedure is used when the balloon has a stent mounted thereon for implanting the stent in the body lumen. The catheter of the invention is useful in a variety of applications including dilatation and stent delivery, and is particularly useful in coronary and neurovascular applications and other applications requiring a low profile, high inflation pressure catheter with excellent maneuverability.

To the extent not previously discussed herein, the various catheter components may be formed and joined by conventional materials and methods. Outer tubular member 14 can be formed by conventional techniques, such as by extruding and necking materials found useful in intravascular catheters such a polyethylene, polyvinyl chloride, polyesters, polyamide, polyimides, polyurethanes, and composite materials. In one presently preferred embodiment, outer tubular member 14 is a nylon.

The length of the dilatation catheter 10 is generally about 137 to about 145 centimeters, and typically about 140 centimeters for PTCA. The outer tubular member 14 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14 proximal section has an OD of about 0.017 to about 0.034 inch (0.43–0.87 mm), and an inner diameter (ID) of about 0.012 to about 0.022 inch (0.30–0.56 mm). The inner tubular member 16 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 24 is typically about 8 to about 38 mm in length, with an inflated working diameter of about 1.5 to about 5 mm.

While the present invention has been described herein in terms of certain preferred embodiments, those skilled in the art will recognize that modifications and improvements may be made without departing from the scope of the invention. For example, while discussed primarily in terms of a balloon catheter, the coil supported shaft may be used in a variety of catheters including guiding catheters, drug delivery catheters, and the like. Additionally, while the illustrated embodiments of the coil supported tubular member have three layers, it should be understood that in alternative embodiments, the coil supported tubular member has a different number of layers such as less than three layers, and specifically two layers (i.e., an inner and outer layer only). Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having an outer tubular member defining an inflation lumen, and an inner tubular member having an inner surface defining a guidewire lumen, the inner tubular member comprising a polymeric tubular member with at least a section having an inner lubricious layer, an intermediate layer on an outer surface of the inner layer, an outer layer on an outer surface of the intermediate layer, and a coiled support member having coils partially embedded in the inner layer so that the guidewire lumen is defined by an inner exposed surface of the coiled support member together with an inner surface of the inner lubricious layer interspersed between the coils of the coiled support member; and
   b) an inflatable balloon on a distal shaft section having an interior in fluid communication with the inflation lumen and a distal skirt section fusion bonded to the inner tubular member outer layer.

2. The balloon catheter of claim 1 wherein the coiled support member is a wire having a diameter of about 0.0005 to about 0.001 inches.

3. The balloon catheter of claim 1 wherein the coiled support member is a ribbon having a width of about 0.002 to about 0.0075 inches, and a height of about 0.0005 to about 0.001 inches.

4. The balloon catheter of claim 1 wherein the inner tubular member has a wall thickness of about 0.0015 to about 0.004 inches.

5. The balloon catheter of claim 1 wherein the inner layer has a wall thickness of about 0.001 to about 0.003 inches.

6. The balloon catheter of claim 1 wherein the inner layer is formed of high density polyethylene.

7. The balloon catheter of claim 1 wherein the intermediate layer has a wall thickness of about 0.0005 to about 0.001 inches.

8. The balloon catheter of claim 1 wherein the intermediate layer is formed of functionalized polyolefin.

9. The balloon catheter of claim 1 wherein the outer layer has a wall thickness of about 0.0005 to about 0.002 inches.

10. The balloon catheter of claim 1 wherein the outer layer is formed of a polymer selected from the group consisting of polyamide, polyether block amide, and polyurethane.

11. The balloon catheter of claim 1 wherein the inner, intermediate, and outer layers comprise a trilayer extrusion.

12. The balloon catheter of claim 1 wherein the inner layer is about 0.001 to about 0.003 inches thick and the coil is completely embedded therein.

13. The balloon catheter of claim 1 wherein the coiled support member has an intercoil spacing of not greater than about 0.010 inches.

14. The balloon catheter of claim 1 wherein the inner tubular member has a collapse pressure of at least about 25 atm.

15. A method of making an elongated tubular shaft for a balloon catheter, comprising winding a wire or ribbon having a lubricious polymeric coating thereon on a mandrel, and placing at least a section of the mandrel and the wound wire or ribbon thereon in a lumen of a polymeric tubular member and applying heat and pressure thereto with heat shrink tubing around an outer surface of the polymeric tubular member, to form an elongated tubular shaft having an inner lubricious layer defining a lumen of the shaft and having a wall thickness of about 0.001 to about 0.003 inches and formed at least in part by the lubricious polymeric coating on the wire or ribbon, a coiled wire or ribbon embedded in the inner layer, and an outer layer on an outer surface of at least a distal portion of the inner layer and formed by the polymeric tubular member.

16. The method of claim 15 wherein the wire or ribbon is wound such that the coiled wire or ribbon has stacked coils, and the inner lubricious layer is formed by the lubricious polymeric coating on the wire or ribbon, and the polymeric coating on the wire or ribbon has a wall thickness of about 0.0003 to about 0.001 inches.

17. The method of claim 16 wherein the polymeric tubular member is formed of a polymeric material selected from the group consisting of a functionalized polyolefin, and a blend of a polyamide and a functionalized polyolefin, and the polymeric tubular member proximal end is positioned distal to the proximal end of the wound wire or ribbon.

18. The method of claim 15 wherein the wire or ribbon is wound such that the coiled wire or ribbon has spaced apart coils, and the polymeric tubular member comprises a triextrusion of an inner lubricious layer, an intermediate layer, and an outer layer.

19. The method of claim 15 wherein the wire or ribbon is wound such that the coiled wire or ribbon has spaced apart coils, and including providing a lubricious polymeric tubular member formed of the same material as the coating on the wire or ribbon between the wound wire or ribbon and the polymeric tubular member.

* * * * *